United States Patent
Robinson et al.

(10) Patent No.: US 6,488,961 B1
(45) Date of Patent: *Dec. 3, 2002

(54) EFFERVESCENT GRANULES AND METHODS FOR THEIR PREPARATION

(75) Inventors: Joseph R Robinson, Madison, WI (US); James W. McGinity, Austin, TX (US)

(73) Assignee: Ethypharm, Inc. (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/468,513

(22) Filed: Dec. 21, 1999

Related U.S. Application Data

(60) Provisional application No. 60/026,991, filed on Sep. 20, 1996.

(51) Int. Cl.$^7$ .............................. A61K 9/46; A61K 9/16; A61K 9/20
(52) U.S. Cl. ...................... 424/466; 424/43; 424/464; 424/489; 424/44
(58) Field of Search ........................ 424/466, 44, 464, 424/489, 43

(56) References Cited

U.S. PATENT DOCUMENTS

| | | |
|---|---|---|
| 1,262,888 A | 4/1918 | Westlake |
| 3,667,929 A | 6/1972 | Fleming |
| 3,962,417 A | 6/1976 | Howell |
| 4,153,678 A | 5/1979 | Quinlan |
| 4,267,164 A | 5/1981 | Yeh |
| 4,613,497 A | 9/1986 | Chaukin |
| 4,639,368 A | 1/1987 | Niazi |
| 4,687,662 A | 8/1987 | Schobel |
| 4,725,427 A | 2/1988 | Ashmead |
| 4,753,792 A | 6/1988 | Aberg |
| 4,940,588 A | 7/1990 | Sparks |
| 5,055,306 A | 10/1991 | Barry |
| 5,100,674 A | 3/1992 | Ser |
| 5,178,878 A | 1/1993 | Wehling |
| 6,071,539 A | * 6/2000 | Robinson et al. ........... 424/466 |

FOREIGN PATENT DOCUMENTS

| | | |
|---|---|---|
| BE | 664197 | 11/1965 |
| DE | 1938709 | 4/1970 |
| DE | 2020893 | 11/1970 |
| EP | 0189114 | 7/1986 |
| EP | 0190689 | 8/1986 |
| EP | 0217631 | 4/1987 |
| EP | 0396335 | 11/1990 |
| GB | 0003160 | 10/1872 |
| GB | 917456 | 2/1963 |
| GB | 1055854 | 1/1967 |
| GB | 1276839 | 6/1972 |
| GB | 1300998 | 12/1972 |
| GB | 1370766 | 10/1974 |
| GB | 2019844 | 11/1979 |
| GB | 2083997 | 4/1982 |

* cited by examiner

*Primary Examiner*—Jose' G. Dees
*Assistant Examiner*—Mina Haghighatian
(74) *Attorney, Agent, or Firm*—Denise L. Mayfield; Lathrop & Gage L.C.

(57) ABSTRACT

Disclosed here are effervescent granules having a controllable rate of effervescence. In some embodiments, the such granules comprise an acidic agent, an alkaline agent, a pharmacologically active agent, hot-melt extrudable binder capable of forming a eutectic mixture with the acidic agent and, optionally, a plasticizer. The effervescent granules are made by a hot-melt extrusion process. The present invention also provides a thermal heat process for preparing a pharmacologically active agent containing effervescent granule. In certain aspects, the granules contain pharmacologically active agents such as narcotics, antidiarrheal agents, antiviral agents, anxiolytic agents, a cholesterol lowering agent, an alpha adrenergic blocking agent, a phenanthrene derivative. By way of example, some of the narcotics that may be included in the granules and in the process of preparing the granules include, by way of example: phenanthrene derivatives (e.g., morphine sulfate), and morphine derivatives (e.g., hydromorphone hydrochloride).

52 Claims, No Drawings

EFFERVESCENT GRANULES AND METHODS FOR THEIR PREPARATION

The present application claims priority to provisional application No. 60/026,991, filed Sep. 20, 1996.

FIELD OF THE INVENTION

This invention relates to an effervescent composition and a method of preparing same. More specifically, it relates to an effervescent granule having a controllable rate of effervescence, the granule being made by a hot-melt extrusion process.

BACKGROUND OF THE INVENTION AND DESCRIPTION OF THE PRIOR ART

Effervescent granules have found a variety of uses over the years. These include dental compositions containing enzymes, contact lens cleaners, washing powder compositions, beverage sweetening tablets, chewable dentifrices, denture cleaners, surgical instrument sterilizers, effervescent candies, as well as many pharmaceutical formulations such as for analgesics, antibiotics, ergotamines, digoxin, methadone and L-dopa.

Film-coated effervescent granules are known in the art. Polymers such as cellulose acetate phthalate or hydroxypropyl methylcellulose have been used. Such coatings have been introduced in order to increase tablet stability as well as to control dissolution rate and to target particular regions of the gastrointestinal tract.

Hot-melt extrusion as a method of preparing pharmaceutical formulations has previously been disclosed; however, effervescent formulations prepared by hot-melt extrusion are not known.

Hot-melt extrusion processes in the art have generally required extremely elevated temperatures (>150° C.), which temperatures could degrade extruded materials. It has not been appreciated that effervescent compositions, which are inherently heat labile, can be hot-melt extruded without significant degradation or decompaction.

Lindberg (Acta). Pharm. Suec. (1988), 25, 239–246) teaches a continuous wet granulation method for preparing effervescent granules. The process includes the steps: (1) mixing powdered citric acid and $NaHCO_3$ in the hopper of a Baker Perkins cooker extruder and granulating the mixture with ethanol.

U.S. Pat. No. 4,153,678 and British Patent Application Laid-Open No. 2083997 disclose effervescent tablets for addition to animal drinking water, respectively containing levamisole and vitamins or minerals as active components. U.S. Pat. No. 3,667,929 discloses that, an effervescent powdery composition coated by pulverizing active components such as piperazine acid salt, copper sulfate or sodium nitrate, an acid substance and carbonate together with a hydrophobic or a slowly dissolving material, is useful as an agent for addition to animal drinking water or a material for horticultural use.

Effervescence can be defined as the evolution of bubbles of gas in a liquid. As set forth in chapter 6 of Pharmaceutical Dosage Forms: Tablets Volume I, Second Edition. A. Lieberman. ed. 1989, Marcel Dekker, Inc. (the entirety of which is hereby incorporated by reference), effervescent mixtures have been known and used medicinally for many years. As discussed in this text, and as commonly employed, an effervescent tablet is dissolved in water to provide a carbonated or sparkling liquid drink. In such a drink the effervescence helps to mask the taste of medicaments. However, the use of effervescent tablets to prepare a beverage including medicaments, is not convenient. It requires preparatory steps before administration of the drug and also requires the presence of a suitable mixing container.

Effervescent tablets have also been used in the dental area. Westlake, U.S. Pat. No. 1,262,888, Howell, U.S. Pat. No. 3,962,417 and Aberg U.S. Pat. No. 4,753,792 disclose effervescent dentifrice tablets adapted to foam in the mouth of a patient so as to provide a tooth cleansing action.

An effervescent dosage form which incorporates microparticles which are susceptible to rupture upon chewing or which are adapted to provide substantially immediate release of the pharmaceutical ingredients contained in the microparticles is disclosed in U.S. Pat. No. 5,178,878 to Wehling et al. The microparticles comprise a drug encapsulated in a protective material. The microparticles are then mixed with an effervescent agent and then the mixture compressed into tablets.

Kond et al., in U.S. Pat. No. 5,223,246, disclose a water soluble effervescent composition prepared by hot-melting (1) an active component and (2) an acid and a carbonate for effervescent, with (3) a water soluble adjuvant whose melting point is not lower than 40° C., for addition to drinking water. The effervescent composition was prepared by mixing the active agent, the acid, the carbonate and the water soluble adjuvant and then heating the entire mixture to melt the adjuvant and subsequently cooling the mixture to room temperature while stirring to form effervescent particles.

Thus, there is no teaching or suggestion in the art of preparing effervescent granules by hot-melt extrusion. Despite prior efforts towards developments of suitable effervescent granules, there have been unmet needs heretofore for improved effervescent granules having controllable rates of effervescence and for methods for their preparation.

SUMMARY OF THE INVENTION

The present invention provides an effervescent granule having a controllable rate of effervescence prepared by hot-melt extruding (i) an acidic agent, (ii) an alkaline agent, and (iii) a hot-melt extrudable binder which melting or softening point temperature is less than about 150° C. and which is capable of forming a eutectic mixture with the acidic agent. The acidic and alkaline agents should be able to effervesce when placed in an aqueous solution. A formulation according to this aspect of the invention can provide a rate of release of an active ingredient that ranges from immediate to a delayed or controlled release over a prolonged period of many hours.

One aspect of the present invention provides a solid pharmaceutical dosage form adapted for direct oral administration, i.e., for direct insertion into the mouth of a patient. A dosage form according to this aspect of the present invention includes a mixture incorporating a water and/or saliva activated effervescent granule having a controllable rate of effervescence and a therapeutic compound.

According to another aspect of the present invention, it has been found that combination of the effervescent granules with the other ingredients can provide effective taste masking of particularly poor tasting compounds. This aspect of the invention thus provides a dosage form which offers both immediate or extended release and effective taste masking.

The effervescent granules taught herein can be used in pharmaceutical, veterinary, horticultural, household, food, culinary, pesticidal, agricultural, cosmetic, herbicidal, industrial, cleansing, confectionery and flavoring applications.

Formulations incorporating the effervescent granules according to one aspect of the present invention can further include one or more additional adjuvants and/or active ingredients which can be chosen from those known in the art including flavors, diluents, colors, binders, filler, surfactant, disintegrant, stabilizer, compaction vehicles, and non-effervescent disintegrants. The effervescent granules themselves do not generally include therapeutic compounds or other active ingredients.

The present invention also provides a method of preparing an effervescent granule having a controllable rate of effervescence where the method comprises mixing and hot melt extruding a hot-melt extrudable binder and an acidic agent to form a eutectic mixture which eutectic mixture is then mixed and hot-melt extruded with an alkaline agent to form the effervescent granule. The hot-melt extrusion process herein advantageously allows for extremely short exposure times of compounds to elevated temperatures as well as a higher throughput than batchwise hot-melt methods.

In particular embodiments, effervescent granules including a pharmacologically active agent are provided. In some aspects, by way of example, and while not intending to constitute an exclusive list, these pharmacologically active agents may comprise, in at least some embodiments, the following pharmacologically active agents: phenanthrene derivatives (e.g. morphine sulfate), synthetic and non-synthetic antidiarrheal agents (e.g. loperamide hydrochloride). In other embodiments, the pharmacologically active agent may comprise an antiviral agent (e.g. acyclovir), anxiolytic agents (e.g. buspirone), diuretic agents (e.g. hydrochlorthiazide), and morphine derivatives (e.g. hydromorphone hydrochloride). In yet other embodiments, the pharmacologically active agent may comprise antidepressants (e.g. fluoxetine hydrochloride), serotonin agonists (e.g. sumatriptan succinate), levorotatory isomers of thyroxine (e.g. levothyroxine sodium), cholesterol lowering agents (e.g. simvastatin) and alpha adrenergic blocking agents (e.g. ergotamine tartrate). Moreover, it is anticipated that other therapeutic, pharmacologically active and/or analgesic compounds may be used in conjunction with the present formulations of effervescent granules, as well as combinations of the various types and classes of pharmacologically active agents described here.

Additionally, the present invention provides a thermal heat process for preparing an effervescent granule formulation comprising a pharmacologically active agent. In some embodiments, the method comprises combining an acidic agent, a pharmacologically active agent, a hot-melt extrudable binder which can combine with said acidic agent, a pharmacologically active agent, and a plasticizer. The inclusion of a plasticizer in the formulation is optional. The acidic agent, alkaline agent, hot-melt extrudable binder and the optional plasticizer may then be dry blended to form a mixture. The mixture may then be hot-melt extruded to form a eutectic mixture. The effervescent mixture is then hot-melt extruded to form effervescent granules having a controllable rate of effervescence. The mixture is then screened and blended after which said mixture is subjected to compression until tablet form is achieved.

In particular embodiments, a thermal heat process for preparing effervescent granules including a pharmacologically active agent are provided. In some aspects, by way of example, and while not intending to constitute an exclusive list, the pharmacologically active agents that may comprise at least some embodiments of the effervescent granules prepared by the present thermal process include: phenanthrene derivatives (e.g. morphine sulfate), synthetic and non-synthetic antidiarrheal agents (e.g. loperamide hydrochloride). In other embodiments, the pharmacologically active agents may comprise antiviral agents (e.g. acyclovir), anxiolytic agents (e.g. buspirone), diuretic agents (e.g. hydrochlorthiazide), and morphine derivatives (e.g. hydromorphone hydrochloride). In yet other embodiments, pharmacologically active agents may comprise antidepressants (e.g. fluoxetine hydrochloride), serotonin agonists (e.g. sumatriptan succinate), levorotatory isomers of thyroxine (e.g. levothyroxine sodium), cholesterol lowering agents (e.g. simvastatin) and alpha adrenergic blocking agents (e.g. ergotamine tartrate). Moreover, it is anticipated that other therapeutic, pharmacologically active and/or analgesic compounds may be used in conjunction with the present formulations of effervescent granules or combinations thereof.

Other features, advantages and embodiments of the invention will be apparent to those skilled in the art from the following description, examples and appended claims.

DETAILED DESCRIPTION OF THE INVENTION

As used herein, the term "effervescent granules" means granules that consist of an effervescent couple and a suitable hot-melt extrudable binder and that are prepared by hot-melt extrusion. By "effervescent couple" is meant a combination of an acidic agent and an alkaline agent that when combined in the presence of water cause the formation of a gas such as carbon dioxide, oxygen or chlorine dioxide.

The effervescent granules of this invention can be in the state of powder or fine particles to increase the dissolution rate, and preferably a particle size such that 90% or more passes a 16 mesh (1,000μ) screen, and more preferably a particle size such that more than 90% passes a 18 mesh (850 mu m) screen. Generally, the larger the effervescent granule, the longer it will take to completely disintegrate. This is particularly true when there are low levels of effervescent couple present in the granules.

Effervescent Granule Components

As used herein, "effervescence" means the evolution of bubbles of gas from a liquid as the result of a bubble or gas generating chemical reaction. The bubble or gas generating reaction of the effervescent couple in the effervescent granule is most often the result of the reaction of an acidic agent and an alkaline agent. The reaction of these two general classes of compounds produces a gas upon contact with water.

As used herein, the term "acidic agent" refers to any compound or material that can serve as a proton source and can react with the alkaline agent of the invention to form a gas causing a solution containing them to effervesce. The acidic agent can have more than one acid dissociation constant, i.e. more than one acid functional group. The acidic agent can be any organic or inorganic acid in the free acid, acid anhydride and acid salt form. An acidic agent which is in solid state at room temperatures and shows pH 4.5 or lower when saturated into water at room temperatures or its acid alkali metal salts (e.g. sodium salt, potassium salt, etc.) can be employed. As the acidic agent for the effervescent granule, a compound which is not harmful to animals including man is desirably employed. The acidic agent can be tartaric acid, citric acid, maleic acid, fumaric acid, malic acid, adipic acid, succinic acid, lactic acid, glycolic acid, alpha hydroxy acids, ascorbic acid, amino acids and their alkali hydrogen acid salts. And, even in the case of an acid substance such as phosphoric acid or pyrophosphoric acid or other inorganic acids which is liquid or in liquid state at room temperature, when their acid alkali metal salts are solid at room temperature, those acid alkali metal salts can be employed as acidic agents. Among the above-mentioned acidic agents, those having a relatively large acid dissociation constant ($10^3$ or more) and a small hygroscopicity (critical humidity at 30° C. is 40% RH or more) are preferably employed.

It is preferred if the acidic agent can form a eutectic mixture with a binder. Because these acids are directly ingested, their overall solubility in water is less important than it would be if the effervescent granules of the present invention were intended to be dissolved in a glass of water.

As used herein, the term "alkaline agent" means an alkaline compound that releases a gas, or causes a solution to effervesce, when exposed to a proton source such as an acidic agent or water. The alkaline agent can be a carbon dioxide gas precursor, an oxygen gas precursor or a chlorine dioxide gas precursor.

When the alkaline agent is a carbon dioxide precursor, compounds such as carbonate, sesquicarbonate and hydrogencarbonate salts (in this specification, carbonate and hydrogencarbonate, or bicarbonate, are generically referred to as carbonate) of potassium, lithium, sodium, calcium, ammonium, or L-lysine carbonate, arginine carbonate, sodium glycine carbonate, sodium amino acid carbonate can be used. When the alkaline agent is an oxygen gas precursor, compounds such as anhydrous sodium perborate, effervescent perborate, sodium perborate monohydrate, sodium percarbonate and sodium dichloroisocyannurate can be used. When the alkaline agent is a chlorine dioxide ($ClO_2$) precursor, compounds such as sodium hypochlorite and calcium hypochlorite can be used. $ClO_2$ can be used as a chemical sterilizer in cleansing operations.

Where the effervescent agent includes two mutually reactive components, such as an acidic agent and an alkaline agent, it is preferred, although not necessary, that both components react completely. Therefore, a ratio of components which provides for equal amounts of reaction equivalents is preferred. For example, if the acid used is diprotic, then either twice the amount of a mono-reactive carbonate alkaline agent, or an equal amount of a all-reactive alkaline agent should be used for complete neutralization to be realized. However, in other embodiments of the present invention, the amount of either the acidic agent or the alkaline agent can exceed the amount of the other component. This can be useful to enhance taste and/or performance of a tablet containing an overage of either component.

By controlling the relative ratio of acidic agent: alkaline agent, the effervescent granules can be used to regulate the pH of their environment. Thus, the present granules can be used to regulate the pH of body cavities such as the mouth, rectum or vagina.

The ratio of the above-mentioned acidic agent and alkaline agent can also be determined according to the pH required for dissolving an active ingredient included in a formulation containing effervescent granules or upon other conditions which a user can contemplate. When the solubility of the active ingredient increases at the acid side, the pH of the solution is lowered by adding the acidic agent in an amount more than equivalent to the alkaline agent. When the solubility of the active ingredient increases at the basic side, the pH of the solution is raised by adding the alkaline agent in an amount more than equivalent to the acidic agent. In either case, the pH near the acidic agent immediately after the dissolution is low, while the pH near an alkaline agent is high. In a case where the solubility of an active ingredient does not depend on pH, the ratio of an acidic agent and an alkaline agent can be optionally selected.

The amount of carbon dioxide precursor, i.e. alkaline agent, to be incorporated is proportional to the volume of carbon dioxide gas generated. When it is desired to increase the dissolution rate of an active ingredient included in a formulation containing effervescent granules, it can be advantageous to increase the amount of carbon dioxide precursor accordingly, and the amount is usually selected from the range of from about 3% to about 70%, preferably from about 10% to 70% by weight based on the effervescent granule.

An acidic agent and a carbon dioxide precursor are used respectively in a powdery or granular state, usually 90% or more of them being capable of passing through a 100 mesh (150$\mu$) screen. The particle size of the binder used will usually be about 100 mesh (150$\mu$). In any case, it is generally acceptable that the additional amount of either component can remain unreacted.

As used herein, the term "hot-melt extrudable" refers to a compound or formulation that can be hot-melt extruded. A hot-melt extrudable binder is one that is sufficiently rigid at standard ambient temperature and pressure but is capable of deformation or forming a semi-liquid state under elevated heat or pressure. Although the formulation of the invention need not contain a plasticizer to render it hot-melt extrudable, plasticizers of the type described herein can be included.

Examples of hot-melt extrudable binders which can be used in the effervescent granules include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, and combinations of the above and the like. Other binders include, for example, polypropylene glycol, polyoxyethylene-polypropylene copolymer, polyethylene ester, polyethylene sorbitan ester, polyethylene oxide and the like.

Binders may be used in an amount of up to about 60 weight percent and preferably about 3 to about 8 weight percent of the total composition. All binders used in this invention are hot-melt extrudable. While the melting and/or softening point temperatures of these binders usually rise with increase of their molecular weights, preferable ones are those with a melting or softening point temperature less than about 150° C. However, binders having melting or softening points greater than about 150° C. can be used. Hot-melt extrudable binders having a melting or softening point temperature greater than about 150° C. will require use of a plasticizer during hot-melt extrusion such that the binder melting or softening point temperature will be lowered below 150° C. Among the above-mentioned binders, polyethylene glycol is preferable, and that having a molecular weight of about 1000 to 8000 Da is more preferable.

The binder can be used in any form such as powder, granules, flakes or heat-molten liquid. While the amount of binder to be added can be modified, it is usually present in an amount less than about 10% by weight and preferably in the range of about 3–8% by weight of the granule.

By "controllable rate of effervescence" is meant that the rate of effervescence can be controlled such that either a rapid, intermediate or slow rate of effervescence by an effervescent granule is achieved. The rate of effervescence by an effervescent granule is controlled as detailed below.

When referring to the rate of effervescence as "rapid", it is understood that the effervescent granules of the present invention should disintegrate in an aqueous solution in less than 10 minutes, and desirably between about 15 seconds and about 7 minutes. In a particularly preferred embodiment according to the present invention, the effervescent granules should dissolve in an aqueous solution in between about 8 seconds and about 5 minutes. Disintegration time can be approximated by observing the disintegration time of the effervescent granules immersed in water at about 37° C. The disintegration time is the time from immersion to substantially complete the effervescent granules as determined by visual observation. As used in this disclosure the term "complete disintegration" of the effervescent granules refers to the dissolution or disintegration of the effervescent granules. Disintegration times referred to in this disclosure should be understood as determined by the method used herein unless otherwise specified.

When referring to the rate of effervescence as "intermediate," it is understood that the effervescent granules of the invention should disintegrate in an aqueous solution in more than about 10 minutes and less than about 1 hour.

When referring to the rate of effervescence as "slow," it is understood that the effervescent granules of the present invention should disintegrate in an aqueous solution in about 1 hour to about 4 hours.

Control of the rate of effervescence can be achieved by varying the relative amounts of the components in the effervescent granule. Thus, by increasing the amount of hot-melt extrudable binder relative to the total weight of the effervescent granule, a less friable and stronger granule can be generally prepared. Conversely, by decreasing the amount of hot-melt extrudable binder relative to the total weight of the effervescent granule, a more friable or weaker granule can be generally prepared. Hydrophobic binders will generally tend to have a greater impact upon granule hardness than hydrophilic binders.

Generally, forming a eutectic mixture between the acidic agent and the hot-melt extrudable binder before hot-melting extruding with the alkaline agent will yield effervescent granules that are harder and thus slower dissolving than those prepared by hot-melt extruding the binder, acidic agent and alkaline agent components together simultaneously.

Having an excess of either the acidic agent or alkaline agent in the effervescent granule will generally result in increased rate of effervescence when compared to an effervescent granule having the same amounts, on an equivalent basis, of both agents. Regardless of whether either agent is in excess, the total amount of gas produced by an effervescent granule will not exceed the theoretical amount of gas produced by the agent serving as the limiting reagent.

It is possible that including a plasticizer in the present effervescent granules will alter its rate of effervescence. Generally, increasing the amount of plasticizer present will increase or prolong the time of effervescence.

The rate of effervescence can also be controlled by varying the hydrophilicity or hydrophobicity of the hot-melt extrudable binder. Generally, the more hydrophobic the binder, the slower the rate of effervescence. The solubility and rate of dissolution of a hydrophobic binder are important factors to consider as the level of binder in the effervescent granule is increased. For example, one can prepare an effervescent granule having a rapid rate of effervescence by a water soluble hot-melt extrudable binder such as an electrolyte or nonelectrolyte such as xylitol, which can form a eutectic mixture with an appropriate acidic agent during hot-melt extrusion.

Conversely, one can prepare an effervescent granule having a slow rate of effervescence by employing a poorly water soluble hot-melt extrudable binder such as hydrogenated castor oil, lipids, wax, cholesterol, fatty acids or mono-, di- or triglycerides. Additionally, an effervescent granule having an intermediate rate of effervescence can be prepared by employing a binder, or combination of binders, such as those just discussed and optionally a surface active agent or cosolvent that improves wetting or disintegration of the effervescent granule.

Thus, rate of effervescence of the effervescent granule can be controlled by: (1) varying the relative amounts of the components; (2) optionally forming a eutectic mixture between the acidic agent and hot-melt extrudable binder; (3) varying acidic agent: alkaline agent ratio; (4) hydrophilicity vs. hydrophobicity of hot-melt extrudable binder; (5) varying the effervescent couple: hot-melt extrudable binder ratio; and (6) varying the amount of plasticizer present.

It should also be noted that when the effervescent granules are included in a tablet form, the hardness of a tablet may also play a role in disintegration time. Specifically, increasing the hardness of a tablet can increase the disintegration time just as decreasing hardness may decrease disintegration time. The hardness of the tablet can be controlled by the pressure used on the punches to compress the effervescent granule-containing formulation and by the amount of effervescent granules, concentration of effervescent couple, and amounts of drug and other excipients present in the tablet composition.

The effervescent granules of the invention can be included in formulations containing active ingredients and particularly pharmacologically active agents. As used herein, the term "active ingredient" means a therapeutic compound, a flavoring agent, a sweetening agent, a vitamin, cleansing agent and other such compounds for pharmaceutical, veterinary, horticultural, household, food, culinary, pesticidal, agricultural, cosmetic, herbicidal, industrial, cleansing, confectionery and flavoring applications. When the effervescent granules are formulated into tablets, such tablets can also contain coloring agents, non-effervescent disintegrants, lubricants and the like. The effervescent granules of the invention can be formulated in a variety of forms such as a tablet, capsule, suspension, reconstitutable powder and suppository.

When a formulation including the effervescent granules and a therapeutic compound is included in a pharmaceutical tablet, the tablet's size and shape can be adapted for direct oral administration to a patient, such as a human patient. The pharmaceutical tablet is substantially completely disintegrable upon exposure to water and/or saliva. The effervescent granule is present in an amount effective to aid in disintegration of the tablet, and to provide a distinct sensation of effervescence when the tablet is placed in the mouth of a patient.

The effervescent sensation is not only pleasant to the patient but also tends to stimulate saliva production, thereby providing additional water to aid in further effervescent action. The patient should be able to perceive a distinct sensation of "fizzing" or bubbling as the tablet disintegrates in the mouth. To provide this sensation, the amount of effervescent granule in each tablet desirably is arranged to provide about 20 to about 60 $cm^3$ of gas. The "fizzing" sensation substantially enhances the organoleptic effects of the tablet. Thus, the amount of effervescent granule useful in accordance with the present invention is also an amount effective to provide a positive organoleptic sensation to a patient. A "positive" organoleptic sensation is one which is pleasant or enjoyable and which can be perceived readily by a normal human being. Thus, once the tablet is placed in the patient's mouth, it will disintegrate substantially completely without any voluntary action by the patient. Even if the patient does not chew the tablet, disintegration will proceed. Upon disintegration of the tablet, the therapeutic compound, which itself can be particulate, is released and can be swallowed as a slurry or suspension.

The mass of each such pharmaceutical tablet generally should be less than about 2.0 g and preferably less than about 0.5 g. The tablet may include surface markings, cuttings, grooves, letters and or numerals for the purpose of decoration and/or identification. Preferably, the tablet is a compressed tablet. It includes effervescent granules, together with a therapeutic compound and other components. The size of the tablet is also dependent upon the amount of material used. Circular, disk-like tablets desirably have diameters of about 11/16 inch or less, whereas elongated tablets desirably have a long dimension of about 7/8 inch or less.

The amount of effervescent granules of the present invention useful for the formation of tablets, in general, according to the present invention should range from about 2 to about 90% by weight of the final tablet composition, and preferably between about 5 and about 40% by weight thereof. In a more preferred embodiment, the amount of effervescent granule according to the present invention ranges from between about 3 and about 8% by weight of the final tablet composition.

Non-effervescent disintegrants include starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin and tragacanth. Disintegrants can comprise up to about 20 weight percent and preferably between about 2 and about 10 percent of the total weight of the composition.

Coloring agents can include titanium dioxide, and dyes suitable for food such as those known as F.D. & C. dyes and natural coloring agents such as grape skin extract, beet red powder, beta-carotene, annato, carmine, turmeric, paprika, etc. The amount of coloring used can range from about 0.1 to about 3.5 weight percent of the total composition.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors may be present in an amount ranging from about 0.5 to about 3.0 by weight based upon the weight of the composition. Particularly preferred flavors are the grape and cherry flavors and citrus flavors such as orange.

Tablets according to this aspect of the present invention can be manufactured by well-known tableting procedures. In common tableting processes, material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. Various tableting methods are well known to those skilled in the art and not detailed herein.

Materials to be incorporated in the tablets, other than the therapeutic compound and the effervescent granule can, be pretreated to form granules that readily lend themselves to tableting. This process is known as granulation. As commonly defined, "granulation" is any process of size enlargement whereby small particles are gathered together into larger, permanent aggregates to yield a free-flowing composition having a consistency suitable for tableting. Such granulated compositions may have consistency similar to that of dry sand. Granulation may be accomplished by agitation in mixing equipment or by compaction, extrusion or globulation.

As noted in Chapter 6 of Pharmaceutical Dosage Forms, supra, lubricants normally are used in manufacture of effervescent tablets. Without the use of an effective lubricant, tableting by use of high speed equipment would be difficult. Effervescent granulations are inherently difficult to lubricate due to both the nature of the raw materials and the requirement that the tablets disintegrate rapidly.

Lubricant, as used herein, means a material which can reduce the friction arising at the interface of the tablet and the die wall during compression and ejection thereof. Lubricants may also serve to prevent sticking to the punch and, to a lesser extent, the die wall as well. The term "antiadherents" is sometimes used to refer specifically to substances which function during ejection. As used in the present disclosure, however, the term "lubricant" is used generically and includes "antiadherents". Tablet sticking during formation and/or ejection may pose serious production problems such as reduced efficiency, irregularly formed tablets, and non-uniform distribution of intended agents or ingredients to be delivered thereby. These problems are particularly severe with high speed tableting approaches and methods.

Lubricants may be intrinsic or extrinsic. A lubricant which is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity.

Intrinsic lubricants are incorporated in the material to be tableted. Magnesium, calcium and zinc salts of stearic acid have long been regarded as the most efficient intrinsic lubricants in common use. Concentrations of two percent or less are usually effective.

Other traditional intrinsic lubricants include hydrogenated and partially hydrogenated vegetable oils, animal fats, polyethyleneglycol, polyoxyethylene monostearate, talc, light mineral oils, sodium benzoate, sodium lauryl sulphate, magnesium oxide and the like. See European Patent Application No. 0,275,834, the disclosure of which is incorporated by reference. See also Leal, et al., U.S. Pat. No. 3,042,531.

Lubricants, according to the present invention, can be used in an amount of up to 1.5 weight percent and preferably between about 0.25 and about 1.0 weight percent of the total composition.

Intrinsic lubricants pose certain serious difficulties when used in conventional tablets. Many lubricants materially retard the disintegration of non-effervescent tablets. However, the effervescent granules used in the dosage form of the present invention overcome any such retardation. In dissolution of conventional effervescent tablets, the lubricant may cause "scumming" and/or agglomeration.

Stearates, for example leave an objectionable "scum" when an effervescent tablet is placed in a glass of water. This "scum" reduces the aesthetic appeal of the solution made from an effervescent dosage form. However, because the tablets of the present invention dissolve in the mouth, the solution is never seen by the user. Therefore, the propensity of a lubricant to "scum" is of less importance. Thus, lubricants which can cause dissolution or scumming problems in other dosage forms can be used in dosage forms according to the present invention without material adverse effect.

The therapeutic compound included in a dosage form including the effervescent granules according to the invention can include at least one psychotropic drug such as a sedative, antidepressant, neuroleptic, or hypnotic. The present invention is especially valuable with psychotropic drugs in that a patient receiving such drugs, particularly a patient in a mental institution, often attempts to hold a conventional pharmaceutical tablet or capsule concealed within his mouth rather than swallow it. The patient may then surreptitiously remove the tablet or capsule when medical personnel are not present. The preferred dosage forms according to this aspect of the present invention are substantially resistant to such concealment, inasmuch as they will disintegrate rapidly even if they are concealed within the mouth.

As the therapeutic compound, use can be of synthetic antibacterial agents of hardly water-soluble pyridonecarboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof. Other therapeutic compounds which can be formulated along with the effervescent granules into an effervescent solid dosage form include penicillin, tetracycline, erythromycin, cephalosporins and other antibiotics.

The therapeutic compounds which can be formulated in suitable dosage forms along with the effervescent granules of the invention also include antibacterial substances, antihistamines and decongestants, anti-inflammatories, antiparasitics, antivirals, anxiolytic agents, morphine derivatives, serotonin agonists, levorotatory isomers of thyroxine, cholesterol lowering agents, alpha adrenergic blocking agents, local anesthetics, antifungal, amoebicidal, or trichomonocidal agents, analgesics, antiarthritics, antiasthmatics, anticoagulants, anticonvulsants, antidepressants, antidiabetics, antineoplastics, antipsychotics, antihypertensives, phenanthrene derivatives, antidiarrheal agents, diuretics, and muscle relaxants.

Representative antibacterial substances are beta-lactam antibiotics, tetracyclines, chloramphenicol, neomycin, gramicidin, bacitracin, sulfonamides, aminoglycoside antibiotics, tobramycin, nitrofurazone, nalidixic acid and analogs and the antimicrobial combination of fludalanine/pentizidone. A representative phenanthrene derivative is morphine sulfate. A representative antidiarrheal agent is loperamide hydrochloride. A representative anxiolytic agent is buspirone. A representative diuretic agent is hydrochlorthiazide. A representative morphine derivative is hydromorphone hydrochloride. Representative antihistamines and decongestants are perilamine, chlorpheniramine, tetrahydrozoline and antazoline. Representative anti-inflammatory drugs are cortisone, hydrocortisone, betamethasone, dexamethasone, fluocortolone, prednisolone, triamcinolone, indomethacin, sulindac and its salts and corresponding sulfide. A representative antiparasitic compound is ivermectin.

Representative antiviral compounds are acyclovir and interferon. Representative analgesic drugs are diflunisal, aspirin or acetaminophen.

Representative antiarthritics are phenylbutazone, indomethacin, silindac, its salts and corresponding sulfide, dexamethasone, ibuprofen, allopurinol, oxyphenbutazone or probenecid. Representative antiasthma drugs are theophylline, ephedrine, beclomethasone dipropionate and epinephrine. Representative anticoagulants are heparin, bishydroxycoumarin, and warfarin. Representative anticonvulsants are diphenylhydantoin and diazepam. Representative antidepressants are amitriptyline, chlordiazepoxide perphenazine, fluoxetine hydrochloride, protriptyline, imipramine and doxepin. A representative cholesterol lowering agent is simvastatin. A representative alpha adrenergic blocking agent is ergotamine tartrate. A representative serotonin agonist is sumatropin succinate. A representative levorotatory isomer of thyroxine is levothyroxine sodium. Representative antidiabetics are insulin, somatostatin and its analogs, tolbutamide, tolazamide, acetchexamide and chlorpropamide. Representative antineoplastics are adriamycin, fluorouracil, methotrexate and asparaginase. Representative antipsychotics are prochlorperazine, lithium carbonate, lithium citrate, thioridazine, molindone, fluphenazine, trifluoperazine, perphenazine, amitriptyline and trifluopromazine. Representative antihypertensives are spironolactone, methyldopa, hydralazine, clonidine, chlorothiazide, deserpidine, timolol, propranolol, metoprolol, prazosin hydrochloride and reserpine. Representative muscle relaxants are succinylcholine-chloride, danbrolene, cyclobenzaprine, methocarbamol and diazepam.

The therapeutic compound(s) contained within a formulation containing effervescent granules can be formulated as its pharmaceutically acceptable salts. As used herein, "pharmaceutically acceptable salts" refer to derivatives of the disclosed compounds wherein the parent pharmacologically active compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, furnaic, toluenesulfonic, methanesulfonic, ethane disulfonic, oxalic, isethionic, and the like.

The pharmaceutically acceptable salts of the present invention can be synthesized from the parent therapeutic compound which contains a basic or acidic moiety by conventional chemical methods. Generally, such salts can be prepared by reacting the free acid or base forms of these compounds with a predetermined amount of the appropriate base or acid in water or in an organic solvent, or in a mixture of the two. Generally, nonaqueous media are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term vitamin refers to trace organic substances that are required in the diet. For the purposes of the present invention, the term vitamin(s) include, without limitation, thiamine riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (AND), Nicotinamide adenine dinucleotide phosphate (NADP) Coenzyme A (CoA) pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

The amount of therapeutic compound incorporated in each tablet may be selected according to known principles of pharmacy. An effective amount of therapeutic compound is specifically contemplated. By the term effective amount, it is understood that, with respect to for example pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The therapeutic compound is used in finely divided form, i.e. powder or granulate so as to increase the dissolution rate. It is preferable to use a finely powdered therapeutic compound to increase the dissolution rate, more preferably, the therapeutic compound being capable of allowing not less than 80%, desirably not less than 90% of it to pass through a 100 mesh (150 mu m) screen. The amount of therapeutic compound to be incorporated ranges usually from about 0.1 to 50%, preferably about 1 to 25% by weight based on the effervescent composition, and the ratio may be suitably modified depending on the therapeutic compound then employed. When the therapeutic compound is an acid substance capable of effervescing by reaction with carbonate, the therapeutic compound itself may be used as the acidic agent, and, in this case, an acidic agent for use as set forth below may be optionally added farther.

When the effervescent granules of the invention are formulated into a reconstitutable powder for a carbonated beverage, they can be prepared according to Example 4 or other suitable method known to those of skill in the art.

The effervescent granules formulated into a suppository can be used to treat vaginal infection and adjust vaginal pH. Such a formulation can be prepared according to example 5, or other method well known to those of skill in the art.

Suspensions containing the effervescent granules of the invention and a herbicide can be used in agricultural applications. Such formulations can comprise a reconstitute powder according to example 6, which is suspended in a liquid prior to use.

Hot Melt Extrusion

In one aspect of this invention, the effervescent granule is produced by a hot-melt extrusion method as described herein. An acidic agent and an alkaline agent, preferably a carbon dioxide precursor, and a hot-melt extrudable binder, all in a dry state, are placed into a mixer or hopper and agitated (blended) until thoroughly mixed to form an effervescent mixture. The effervescent mixture is then hot-melt extruded at a rate and temperature sufficient to melt or soften the binder, to minimize degradation of the components and to form an extrudant which is subsequently ground or chopped into effervescent granules.

In another aspect of the invention, the effervescent granule is produced by a hot melt extrusion process as follows. An acidic agent and a hot-melt extrudable binder, capable of forming a eutectic mixture with the acidic agent, are placed into a mixer and agitated until thoroughly mixed to form a mixture which is hot-melt extruded and ground to form a granular eutectic mixture. An alkaline agent, such as a carbon dioxide precursor, is added to the granular eutectic mixture and thoroughly blended to form an effervescent mixture. The effervescent mixture is then hot-melt extruded at a rate and temperature sufficient to melt or soften the eutectic mixture, to minimize degradation of the components, e.g. degradation of $NaHCO_3$ to $Na_2CO_3$, and to form an extrudant which is subsequently ground or chopped into effervescent granules.

As used herein, the term "effervescent mixture" means a granular or particulate mixture comprising an acidic agent, an alkaline agent and a hot-melt extrudable binder which when placed in water will cause effervescence. As used herein, the term "eutectic mixture" means a mixture of an acidic agent and a hot-melt extrudable binder that has been hot-melt extruded and that melts or softens at a temperature lower than the melting or softening temperature of the hot-melt extrudable binder neat. The eutectic mixture can be a full or partial mixture and can be referred to as a "solid solution."

The rate at which the hot-melt extrusion is conducted can also vary widely. The rate will be such that degradation of the components of the mixture being extruded will be minimized. Such rate can be easily determined experimentally and will vary according to the particular mixture being extruded. Generally, the extrusion rate is such that the time of exposure of the components to the elevated temperature is less than 5 minutes and preferably less than 2 minutes.

The rate of effervescence can be controlled by varying the rate of hot-melt extrusion. Generally, increasing the rate of hot-melt extrusion of the effervescent granule will increase the rate of effervescence. This is especially true for hot-melt extrudable binders having melting or softening points greater than about 100 C. Conversely, decreasing the rate of hot-melt extrusion of effervescent granule will generally decrease the rate of effervescence.

The hot-melt extrusion process preferably employed is conducted at an elevated temperature, i.e. the heating zone (s) of the extruder is above room temperature (about 20° C.). It is important to select an operating temperature range that will minimize the degradation or decomposition of the effervescent composition during processing. The operating temperature range is generally in the range of from about 50° C. to about 150° C. as determined by the setting for the extruder heating zone(s). The temperature of the mixture being hot-melt extruded will not exceed 150° C. and preferably will not exceed 120° C. The hot-melt extrusion is conducted employing a dry granular or powdered feed.

The extruder used to practice the invention can be any such commercially available model equipped to handle dry feed and having a solid conveying zone, one or multiple heating zones, and an extrusion die. A two stage single screw extruder, such as that manufactured by BRABENDER or KILLION are two such apparati. It is particularly advantageous for the extruder to possess multiple separate temperature controllable heating zones.

Many conditions can be varied during the extrusion process to arrive at a particularly advantageous formulation. Such conditions include, by way of example, formulation composition, feed rate, operating temperature, extruder screw RPM, residence time, die configuration, heating zone length and extruder torque and/or pressure. Methods for the optimization of such conditions are known to the skilled artisan.

When higher melting temperature, higher molecular weight or high softening temperature binders are employed, the hot-melt extrusion may require higher processing temperature, pressure and/or torque than when binders having a lower molecular weight, melting or softening temperature are employed. By including a plasticizer, and, optionally, an antioxidant, in a formulation, processing temperature, pressure and/or torque may be reduced. Plasticizers are not required in order to practice the invention. Their addition to the formulation is contemplated as being within the scope of the invention. Plasticizers are advantageously included in the effervescent granules when hot-melt extrudable binders having a melting or softening point temperature greater than 150° C. are employed.

As used herein, the term "plasticizer" includes all compounds capable of plasticizing the hot-melt extrudable binder of the invention. The plasticizer should be able to lower the melting temperature or glass transition temperature (softening point temperature) of the hot-melt extrudable binder. Plasticizers, such as low molecular weight PEG, generally broaden the average molecular weight of the hot-melt extrudable binder thereby lowering its glass transition temperature or softening point. Plasticizers also generally reduce the viscosity of a polymer melt thereby allowing for lower processing temperature and extruder torque during hot-melt extrusion. It is possible the plasticizer will impart some particularly advantageous physical properties to the effervescent granules.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin.

Such plasticizers can also be ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co.

It is contemplated and within the scope of the invention, that a combination of plasticizers may be used in the present formulation. One advantageous combination is that comprised of poly(ethylene glycol) and low molecular weight poly(ethylene oxide). The PEG based plasticizers are available commercially or may be made by a variety of methods, such as disclosed in *Poly(ethylene glycol) Chemistry: Biotechnical and Biomedical Applications* (J. M. Harris, Ed.; Plenum Press, N.Y.) the teachings of which are hereby incorporated by reference.

The amount of plasticizer used in the effervescent granules will depend upon its composition, physical properties, effect upon the effervescent granules, interaction with other components of the granules and other such reasons. Generally, the plasticizer content will not exceed about 40% wt. of the formulation.

DESCRIPTION OF THE PREFERRED EMBODIMENTS

One embodiment of the present invention provides an effervescent granule having
    a controllable rate of effervescence comprising:
        a hot-melt extrudable binder present in the amount of about 3% to about 8% by weight of said effervescent granule, said binder being capable of forming a eutectic mixture with an acidic agent;
        an acidic agent; and
        an alkaline agent; said effervescent granule being made by a process comprising:
            dry blending and hot-melt extruding said acidic agent and said hot-melt extrudable binder to form an acidic mixture; and
            dry blending and hot-melt extruding the acidic mixture and said alkaline agent to form said effervescent granule.

Another embodiment of the present invention provides a hot-melt extrusion process for preparing an effervescent granule having a controllable rate of effervescence, said process comprising:
    dry blending and hot-melt extruding an acidic agent, a hot-melt extrudable binder and a plasticizer to form a eutectic mixture; and
    dry blending and hot-melt extruding the eutectic mixture and an alkaline agent to form said effervescent granule.

The foregoing will be better understood with reference to the following examples which detail certain procedures for the manufacture of tablets according to the present invention. All references made to these examples are for the purposes of illustration. They are not to be considered limiting as to the scope and nature of the present invention.

EXAMPLE 1

Effervescent Granule Formulation (MS-EGF) Prepared by Hot Melt Extrusion

The present example is provided to demonstrate the utility of the present invention for the preparation of a fast melt tablet formulation that included one or more narcotics. Morphine sulfate is the example of the narcotic provided as part of the present example. As will be understood by those of ordinary skill in the art, components that are reasonably equivalent to these for purposes of pharmaceutical agent preparation may be used in substitution of the specifically developed ingredients below.

| Ingredient | Amount (% Wt.) |
| --- | --- |
| Morphine Sulfate | 24 |
| Sodium Bicarbonate | 27 |
| Citric Acid, Arihydrous | 27 |
| Microcrystalline Cellulose | 10 |
| Xylitol | 10 |
| Sucrose Stearate | 2 |

Category B
  Morphine Sulfate Tablet Foundation
  Formulation 1:

| Ingredient | Amount (% Wt.) |
| --- | --- |
| MS-EGF (30-60 mesh) | 50 |
| Microcrystalline Cellulose | 31 |
| Mannitol | 10 |
| AcDiSol | 5 |
| Aspartame | 3 |
| Redberry Flavor | 0.4 |
| Magnesium Stearate | 0.5 |
| Cab-O-Sil M5P | 0.1 |

Formulation 2:

| Ingredient | Amount (% Wt.) |
| --- | --- |
| MS-EFG (30-60 mesh) | 50 |
| Microcrystalline Cellulose | 31 |
| Mannitol | 10 |
| L-HPC LH-11 | 5 |
| Aspartame | 3 |
| Redberry flavor | 0.4 |
| Magnesium Stearate | 0.5 |
| Cab-O-Sil M5P | 0.1 |

Formulation 3:

| Ingredient | Amount (% Wt.) |
| --- | --- |
| MS-EFG (20-80 mesh) | 50 |
| Anhydrous Lactose | 18 |
| Fujicalin SG | 18 |
| L-HPC LH-11 | 3 |
| Aspartame | 0.3 |
| Natural Orange Powder | 0.3 |
| Magnesium Stearate | 0.6 |
| Fumed Silicon Dioxide | 0.1 |

The morphine sulfate in the effervescent granulation formulation is dried at 100° C. for 2–4 hours to reduce the moisture content of the material. Other ingredients are dried at 40° 60° C. to significantly reduce the moisture content of the material.

The ingredients in Category A were then blended for 10 minutes and extruded in a hot melt extruder at 70°–100° C. to soften and melt the thermal binders (sucrose stearate and xylitol) and to form granules containing the effervescent couple.

Granules were then screened and blended with the ingredients in Category B for 5 minutes prior to compression. Morphine sulfate tablets from Formulations #1, #2 or #3 are then compressed to a hardness of approximately 1–5 kg and tablets disintegrate in water in approximately 15–35 seconds. Tablet size, hardness and disintegration times will vary with slight modifications in the formulation. The dose of the morphine sulfate may be varied by varying the amount and/or form of the drug to be included in the formulation.

EXAMPLE 2

Loperamide HCl Fast Melt Tablet Formulation

The present example is provided to demonstrate the utility of the present invention for the preparation of formulations useful in treating gastrointestinal disorders, such as diarrhea. Loperamide HCl is employed in the present example, and is only one of many potential agents that may be used.

Category A
  Effervescent Granule Formulation (LH-EGF)
  Prepared by Hot Melt Extrusion

| Ingredient | Amount (% Wt.) |
| --- | --- |
| Loperamide Hydrochloride | 5 |
| Sodium Bicarbonate | 27 |
| Citric Acid Anhydrous | 27 |
| Tartaric Acid | 3 |
| Microcrystalline Cellulose | 15 |
| Anhydrous Lactose | 8 |
| Xylitol | 12 |
| Crodesta F160 | 3 |

Category B
  Loperamide Hydrochloride Tablet Formulation

| Ingredient | Amount (% Wt.) |
| --- | --- |
| LH-EFG (30-80 mesh) | 50 |
| Microcrystalline Cellulose | 31 |
| Mannitol | 8 |
| AcDiSol | 5 |
| L-HPC LH-11 | 2 |
| Aspartame | 3 |
| Redberry Flavor | 0.4 |
| Magnesium Stearate | 0.5 |
| Cab-O-Sil M5P | 0.1 |

The ingredients in Category A are dried at elevated temperature in the presence of a dessicant to significantly reduce the moisture content of each material.

The ingredients are then blended for 10 minutes and extruded in a hot melt extruder at 70°–100° C. to soften and melt the thermal binders (sucrose stearate and xylitol) to form granules containing the effervescent couple Granules are passed through a screen and then blended with the ingredients in Category B for 5 minutes prior to compression. Loperamide FICI tablets are then compressed to a hardness of approximately 1–3 kg and tablets disintegrate in purified water in approximately 15–35 seconds.

EXAMPLE 3

Acyclover (200 MG) Antiviral Fast Melt Tablets

The present example is provided to demonstrate the utility of the present invention for the preparation of antiviral formulations. Acyclovir is employed in the present example and is only one of the therapeutic agents which can be formulated in suitable dosage forms along with the effervescent granules of the invention.

Category A

Effervescent Granule Formulation (ACY-EFG)
Prepared by Hot Melt Extrusion

| Ingredient | Amount (% Wt.) |
| --- | --- |
| Acyclovir | 50 |
| Sodium Bicarbonate | 18 |
| Citric Acid Anhydrous | 18 |
| Anhydrous Lactose | 7 |
| Xylitol | 5 |
| Crodesta F160 | 2 |

Category B

Acyclovir Tablet Formulation

| Ingredient | Amount (% Wt.) |
| --- | --- |
| ACY-EFG (30-60 mesh) | 50 |
| Microcrystalline Cellulose | 18 |
| Fujicalin SG | 18 |
| L-HPC LH-11 | 10 |
| Aspartame | 3 |
| Redberry Flavor | 0.4 |
| Magnesium Stearate | 0.5 |
| Cab-O-Sil M5P | 0.1 |

The ingredients in Category A are dried to significantly reduce the moisture content of each material.

The ingredients are then blended for 10 minutes and extruded in a hot melt extruder at 70°–100° C. to soften and melt the thermal binders (sucrose stearate and xylitol) to form granules containing the effervescent couple.

Granules are then screened and blended with the ingredients in Category B for 5 minutes prior to compression. Acyclovir tablets are then compressed to a hardness of approximately 1–3 kg and tablets disintegrate in water in approximately 20–45 seconds.

EXAMPLE 4

Buspirone (5 MG) Anxiolytic Fast Melt Tablets

The present example is provided to demonstrate the utility of the present invention for the preparation of hydrochloride formulations useful in treating mild anxiety disorders. Buspirone is employed in the present example, such drug being characterized by its tendency against inducing significant tolerance or psychological dependence.

Category A

Effervescent Granule Formulation (BUS-EGF)
Prepared by Hot Melt Extrusion

| Ingredient | Amount (% Wt.) |
| --- | --- |
| Buspirone | 8 |
| Sodium Bicarbonate | 25 |
| Citric Acid Anhydrous | 25 |
| Avicel PH113 | 12 |
| Anhydrous Lactose | 17 |
| Xylitol | 11 |
| Crodesta F160 | 2 |

Category B

Buspirone Tablet Formulation

| Ingredient | Amount (% Wt.) |
| --- | --- |
| BUS-EGF (20-80 mesh) | 50 |
| Microcrystalline Cellulose (Avicel PH 113) | 31 |
| Mannitol (Mannogen 3215) | 10 |
| AcDiSol | 5 |
| Aspartame | 3 |
| Redberry Flavor | 0.4 |
| Magnesium Stearate | 0.5 |
| Fumed Silicon Dioxide | 0.1 |

Ingredients in Category A are dried at 40°–60° C. to significantly reduce the moisture content of each material.

The ingredients in Category A were then blended for 10 minutes and extruded in a hot melt extruder at 70°–100° C. to soften and melt the thermal binders (sucrose stearate and xylitol) and to form granules containing the effervescent couple.

Granules were then screened and blended with the ingredients in Category B for 5 minutes prior to compression. Buspirone tablets were then compressed to a hardness of approximately 1–3 kg and tablets disintegrate in water in approximately 15–35 seconds.

EXAMPLE 5

Hydrochlorthiazide (25 MG) Fast Melt Tablets-Diuretic

The present example is provided to demonstrate the utility of the present invention for the preparation of diuretic formulations useful in treating hypertension. Hydrochlorthiazide is the therapeutic drug employed in the present example.

Category A

Effervescent Granule Formulation (HYD-EFG)
Prepared by Hot Melt Extrusion

| Ingredient | Amount (% Wt.) |
| --- | --- |
| Hydrochlorthiazide | 20 |
| Sodium Bicarbonate | 25 |
| Citric Acid Anhydrous | 25 |
| Avicel PH113 | 18 |
| Xylitol | 10 |
| Crodesta F160 | 2 |

Category B
  Hydrochlorthiazide Tablet Formulation

| Ingredient | Amount (% Wt.) |
| --- | --- |
| HYD-EFG (30-60 mesh) | 50 |
| Microcrystalline Cellulose | 31 |
| Anhydrous Lactose | 10 |
| AcDiSol | 2.5 |
| L-HPC LH-11 | 2.5 |
| Aspartame | 3 |
| Redberry Flavor | 0.4 |
| Magnesium Stearate | 0.5 |
| Cab-O-Sil M5P | 0.1 |

The ingredients are dried at elevated temperatures to significantly reduce the moisture content of each material.

The ingredients in Category A were then blended for 10 minutes and extruded in a hot melt extruder at 70°–100° C. to soften and melt the thermal binders (sucrose stearate and xylitol) and to form granules containing the effervescent couple.

Granules are then screened and then blended with the ingredients in Category B for 5 minutes prior to compression. Hydrochlorthiazide tablets were then compressed to a hardness of approximately 1–3 kg and tablets disintegrate in water in approximately 15–35 seconds.

EXAMPLE 6

Hydromorphone Hydrochloride (8 MG) Fast Melt Tablets for Pain

The present example is provided to demonstrate the utility of the present invention for the preparation of formulations useful in alleviating physical pain. Hydromorphone hydrochloride, which is most useful as an analgesic in its hydrochloride salt form, is employed in the present example.

Category A
  Effervescent Granule Formulation (HDM-EGF)

| Ingredient | Amount (% Wt.) |
| --- | --- |
| Hydromorphine Hydrochloride | 15 |
| Sodium Bicarbonate | 28 |
| Citric Acid Anhydrous | 24 |
| Microcrystalline Cellulose | 10 |
| Anhydrous Lactose | 11 |
| Xylitol | 10 |
| Sucrose Stearate | 2 |

Category B
  Hydromorphine Hydrochloride Tablet Formulation

| Ingredient | Amount (% Wt.) |
| --- | --- |
| HDM-EGF (30-60 mesh) | 50 |
| Microcrystalline Cellulose | 18 |
| Anhydrous Lactose | 18 |
| Cross Povidone | 5 |
| L-HPC LH-11 | 5 |
| Aspartame | 3.25 |
| Natural Orange Powder | 0.15 |
| Magnesium Stearate | 0.45 |
| Fumed Silicon Dioxide | 0.15 |

The ingredients in Category A are dried at elevated temperatures to significantly reduce the moisture content of the material.

These ingredients were then blended for 10 minutes and extruded in a hot melt extruder at 70°–100° C. to soften and melt the thermal binders (sucrose stearate and xylitol) and to form granules containing the effervescent couple.

Granules were then screened and blended with the ingredients in Category B for 5 minutes prior to compression. Hydromorphone tablets were then compressed to a hardness of approximately 1–5 kg (depending upon the dose of the active) and tablets disintegrate in water in approximately 15–35 seconds.

EXAMPLE 7

Fluoxetine Hydrochloride (20 MG) Fast Melt Tablet Formulation to Treat Depression The present example is provided to demonstrate the utility of the present invention for the preparation of fast melt tablet formulations useful in treating depression. Fluoxetine hydrochloride, which has its antidepressant effect via the enhancement of serotonin activity, is employed in the present example.

Category A
  Effervescent Granule Formulation (FLX-EFG)
  Prepared by Hot Melt Extrusion

| Ingredient | Amount (% Wt.) |
| --- | --- |
| Fluoxetine Hydrochloride | 18 |
| Sodium Bicarbonate | 26 |
| Citric Acid Anhydrous | 26 |
| Microcrystalline Cellulose | 4 |
| Anhydrous Lactose | 13 |
| Xylitol | 10 |
| Crodesta F160 | 3 |

Category B
  Fluoxetine Hydrochloride Tablet Formulation

| Ingredient | Amount (% Wt.) |
| --- | --- |
| FLX-EFG (20–80 mesh) | 50 |
| Anhydrous Lactose | 31 |
| Microcrystalline Cellulose | 10 |
| L-HPC LH-11 | 5 |
| Aspartame | 3 |
| Redberry Flavor | 0.4 |
| Magnesium Stearate | 0.5 |
| Fumed Silicon Dioxide | 0.1 |

The ingredients in Category A are dried at an elevated temperature to significantly reduce the moisture content of each material.

The ingredients were then blended for 5–10 minutes and extruded in a hot melt extruder at approximately 70°–100° C. to soften and melt the thermal binders (sucrose stearate and xylitol) and to form granules containing the effervescent couple.

The granules were then screened and blended with the ingredients in Category B for 5 minutes prior to compression. Fluoxethine HCl tablets were then compressed to a hardness of approximately 1–5 kg (depending upon the dose of the active) and tablets disintegrate in water in approximately 15–40 seconds.

EXAMPLE 8

Sumatriptan Succinate (6 MG) Fast Melt Tablet Formulation to Treat Migtaine

The present example is provided to demonstrate the utility of the present invention for the preparation of succinate formulations useful in the treatment of migraine headaches. Sumatriptan succinate, a serotonin agonist, is employed in the present example and is administered via injection in its succinate form.

Category A

Effervescent Granule Formulation (SS-EGF)
Prepared by Hot Melt Extrusion

| Ingredient | Amount (% Wt.) |
|---|---|
| Sumatriptan Succinate | 15 |
| Sodium Bicarbonate | 27 |
| Citric Acid Anhydrous | 26 |
| Microcrystalline Cellulose | 11 |
| Anhydrous Lactose | 9 |
| Xylitol | 10 |
| Sucrose Stearate | 2 |

Category B

Sumatriptan Succinate Tablet Formulation

| Ingredient | Amount (% Wt.) |
|---|---|
| SS-EGF (30–60 mesh) | 50 |
| Microcrystalline Cellulose | 31 |
| Mannitol | 10 |
| L-HPC LH-11 | 5 |
| Aspartame | 3 |
| Redberry Flavor | 0.3 |
| Natural Orange Powder | 0.1 |
| Magnesium Stearate | 0.5 |
| Fumed Silicon Dioxide | 0.1 |

The ingredients are dried at elevated temperatures to significantly reduce the moisture content of the materials.

The ingredients were then blended for approximately 10 minutes and extruded in a hot melt extruder at 70°–100° C. to soften and melt the thermal binders (sucrose stearate and xylitol) and to form granules containing the effervescent couple.

Granules were then screened and then blended with the ingredients in Category B for 5 minutes prior to compression. Sumatriptan succinate tablets were then compressed to a hardness of approximately 1–5 kg (depending upon the dose of the active) and tablets disintegrate in water in approximately 15–35 seconds.

EXAMPLE 9

Levothyroxine Sodium (25 MG) Fast Melt Tablets for Diminished thyroid Function

The present example is provided to demonstrate the utility of the present invention for the preparation of formulations useful in treating hypothyroidism. Levothyroxine sodium, tablets of which are indicated as replacement or substitution therapy for diminished or absent thyroid function, is employed in the present example.

Category A

Effervescent Granule Formulation (LS-EGF)
Prepared by Hot Melt Extrusion

| Ingredient | Amount (% Wt.) |
|---|---|
| Levothyroxine Sodium | 30 |
| Sodium Bicarbonate | 24 |
| Citric Acid Anhydrous | 24 |
| Anhydrous Lactose | 10 |
| Xylitol | 10 |
| Sucrose Stearate | 2 |

Category B

Levothyroxine Sodium Tablet Formulation

| Ingredient | Amount (% Wt.) |
|---|---|
| LS-EGF (20–80 mesh) | 55 |
| Microcrystalline Cellulose | 26 |
| Mannitol | 10 |
| Cross Povidone | 5 |
| Aspartame | 3 |
| Redberry Flavor | 0.4 |
| Magnesium Stearate | 0.5 |
| Fumed Silicon Dioxide | 0.1 |

The ingredients in Category A are dried at elevated temperatures to significantly reduce the moisture content of each material.

The ingredients were then blended for 10 minutes and extruded in a hot melt extruder at 70°–100° C. to soften and melt the thermal binders (sucrose stearate and xylitol) and to form granules containing the effervescent couple.

Granules were then reduced in size and blended with the ingredients in Category B for approximately 5 minutes prior to compression. Levothyroxine sodium tablets were then compressed to a hardness of approximately 1–5 kg (depending upon the dose of the drug) and tablets disintegrate in water in approximately 15–35 seconds.

EXAMPLE 10

Simvastatin (10 MG) Fast Melt Tablets to Lower Cholesterol

The present example is provided to demonstrate the utility of the present invention for the preparation of fast melt tablet formulations usefull in treating high cholesterol. Simvastatin, a synthetically derived cholesterol lowering agent, is employed in the present example.

Category A

Effervescent Granule Formulation (SV-EGF)

| Ingredient | Amount (% Wt.) |
|---|---|
| Simvastatin | 15 |
| Sodium Bicarbonate | 25 |
| Citric Acid Anhydrous | 25 |
| Xylitol | 12 |
| Microcrystalline Cellulose | 15 |
| Anhydrous Lactose | 6 |
| Crodesta F160 | 2 |

Category B

Simvastatin Tablet Formulation

| Ingredient | Amount (% Wt.) |
|---|---|
| SV-EGF (30–80 mesh) | 45 |
| Avicel PH113 | 31 |
| Mannogen 3215 | 15 |
| L-HPC LH-11 | 5 |
| Aspartame | 3 |
| Redberry Flavor | 0.25 |
| Natural Orange Powder | 0.15 |
| Magnesium Stearate | 0.5 |
| Fumed Silicon Dioxide | 0.1 |

The ingredients in Category A are dried at elevated temperature in the presence of a dessicant to significantly reduce the moisture content of each material.

These ingredients were then blended for 10 minutes and extruded in a hot melt extruder at 70°–100° C. to soften and melt the thermal binders (sucrose stearate and xylitol) and to form granules containing the effervescent couple.

Granules were reduced in size and then, blended with the ingredients in Category B for 5 minutes prior to compression. Simvastatin tablets were then compressed to a hardness of approximately 1–5 kg (depending upon the dose of the drug) and tablets disintegrate in water in approximately 15–35 seconds.

EXAMPLE 11

Ergotamine Tartrate (2 MG) Fast Melt Tablets to Treat Migraine

The present example is provided to demonstrate the utility of the present invention for the preparation of a fast melt tablet formulation effective in the treatment of migraine headaches. Ergotamine tartrate, an alpha adrenergic blocking agent which produces depression of central vasomotor centers, is the therapeutic drug employed in the present example.

Category A

Effervescent Granule Formulation (EGT-EGF)

Prepared by Hot Melt Extrusion

| Ingredient | Amount (% Wt.) |
|---|---|
| Ergotamine Tartrate | 10 |
| Sodium Bicarbonate | 27 |
| Citric Acid Anhydrous | 22 |
| Avicel PH113 | 15 |
| Xylitol | 15 |
| L-HPC LH-11 | 5 |
| Fujicalin SG | 4 |
| Crodesta F160 | 2 |

Category B

Ergotamine Tartrate Tablet Formulation

| Ingredient | Amount (% Wt.) |
|---|---|
| EGT-EGF (20–80 mesh) | 55 |
| Microcrystalline Cellulose | 26 |
| Mannitol | 10 |
| AcDiSol | 2.5 |
| L-HPC LH-11 | 2.5 |
| Aspartame | 3 |
| Redberry Flavor | 0.4 |
| Magnesium Stearate | 0.5 |
| Fumed Silicon Dioxide | 0.1 |

The ingredients in Category A were dried to significantly reduce the moisture content of each material.

These ingredients were then blended for 10 minutes and extruded in a hot melt extruder to soften and melt the thermal binders (sucrose stearate and xylitol) and to form granules containing the effervescent couple.

Granules were then passed through a #20 screen and then blended with the ingredients in Category B for 5 minutes prior to compression. Ergotamine tartrate tablets were then compressed to a hardness of approximately 1–5 kg and tablets disintegrate in water in approximately 15–35 seconds.

EXAMPLE 12

Preparation of Effervescent Granules

The following general procedure can be used to prepare a variety of effervescent granules according to the present invention.

All materials to be used are passed through a fine screen (100 mesh). The materials are then dried at 40° C. for 24 hours, preferably in a vacuum. The following steps are conducted in an atmosphere having a low relative humidity. All materials are then mixed in a twin shell blender for 5–10 minutes until a uniform blend is achieved. Then, using a hot-melt extrusion apparatus, the powder blend is subjected to a temperature of less than or equal to about 120° C. at a rate and for a period of time sufficient to melt or soften the binder to form agglomerates of the effervescent couple in an extrudant which is either chopped or ground. The extruded granules are then screened and stored at a low relative humidity for subsequent incorporation into a variety of pharmaceutical dosage forms.

The following materials can be used to prepare the effervescent granules according to the procedure just described.

| Ingredient | Amount (% Wt.) |
|---|---|
| A. | |
| NaHCO$_3$ | 52 |
| Citric Acid | 14 |
| Tartaric Acid | 28 |
| PEG 1,000 | 6 |
| B. | |
| NaHCO$_3$ | 55 |
| Citric Acid | 13.5 |
| Tartaric Acid | 24 |
| PEG 4,000 | 7.5 |
| C. | |
| Sodium Glycine Carbonate | 58 |
| Citric Acid | 15 |
| Tartaric Acid | 21 |
| Pluronic F68 | 6 |

-continued

| Ingredient | Amount (% Wt.) |
|---|---|
| D. | |
| NaHCO$_3$ | 54 |
| Citric Acid | 16 |
| Tartaric Acid | 24 |
| PEG 20,000 | 3 |
| PEG 400 | 3 |
| E. | |
| NaHCO$_3$ | 50 |
| Citric Acid | 14 |
| Tartaric Acid | 28 |
| PEG 8,000 | 8 |
| F. | |
| KHCO$_3$ | 62 |
| Fumaric Acid | 5 |
| Citric Acid | 8 |
| Tartaric Acid | 18 |
| PEG 6,000 | 7 |
| G. | |
| NaHCO$_3$ | 55 |
| NaH$_2$PO4 | 37.5 |
| Pluronic F127 | 75 |
| H. | |
| NaHCO$_3$ | 54 |
| Fumaric Acid | 3 |
| Maleic Acid | 5 |
| Citric Acid | 13 |
| Tartaric Acid | 18 |
| PEG 3,350 | 6 |
| Pluronic F68 | 4 |
| I. | |
| NaHCO$_3$ | 56 |
| Citric Acid | 37 |
| Cetyl alcohol | 4 |
| Stearyl alcohol | 5 |
| J. | |
| NaHCO$_3$ | 51 |
| Citric Acid | 34 |
| Xylitol | 15 |
| K | |
| NaHCO$_3$ | 50 |
| Citric Acid | 40 |
| Xylitol | 10 |

In example K, xylitol and citric acid are first hot melt extruded to form a eutectic mixture which is then hot melt extruded with NaHCO$_3$ to form the effervescent granule.

Table 1 is presented to demonstrate the utility of the present invention as used together with granules that effervesce relatively rapidly in the presence of water. These granules may then be formulated into a tablet or other dose compatible and convenient form. These granules are to be prepared by hot melt extrusion as described herein, as well as modified processes thereof.

TABLE 1

Rapidly effervescent granules in contact with water.
HME-EC Granulations

| Excipient | Formulation L % w/w | Formulation M % w/w | Formulation N % w/w | Formulation O % w/w |
|---|---|---|---|---|
| PEG 3350 | 10 | 10 | 10 | 10 |
| Sodium Bicarbonate | 10 | 10 | 10 | 10 |
| Sodium Carbonate, fine powder | 30 | 0 | 0 | 0 |
| Potassium Carbonate, fine powder | 0 | 25 | 28 | 30 |
| Citric Acid, anhydrous | 40 | 35 | 37 | 40 |
| Xylitol, granular | 0 | 0 | 8 | 10 |
| Xylitol, fine powder | 0 | 10 | 0 | 0 |
| Kollodion ® CL | 10 | 10 | 0 | 0 |
| AcDiSol ® | 0 | 0 | 7 | 0 |

Table 2 is presented to demonstrate the utility of the above described rapidly effervescence granules that contain xylitol. These granules are prepared by a hot-melt extrusion process.

TABLE 2

HME-EC Granules With Xylitol

| Excipient | Formulation P % w/w | Formulation Q % w/w | Formulation R % w/w | Formulation S % w/w |
|---|---|---|---|---|
| PEG 3350 | 6.5 | 6.5 | 6.5 | 6.5 |
| Sodium Bicarbonate | 10 | 10 | 10 | 10 |
| Sodium Carbonate, fine powder | 30 | 0 | 0 | 0 |
| Potassium Carbonate, fine powder | 0 | 25 | 28 | 30 |
| Citric Acid, anhydrous | 40 | 35 | 37 | 40 |
| Xylitol, granular | | 3.5 | 8 | 10 |
| Xylitol, fine powder | 3.5 | 10 | 3.5 | 3.5 |
| Kollodion ® CL | 10 | 10 | 0 | 0 |
| AcDiSol ® | 0 | 0 | 7 | 0 |

EXAMPLE 13

Determination of Effervescent Granule Dissolution Rate

This is a visual end-point test for determining effervescent granule solubility.

Effervescent granules (2.0 grams) were added rapidly in one portion to a very gently stirred (less than 60 rpm) beaker containing water (1.0 L) at about 20°–25° C. The endpoint was visually determined by observing cessation of effervescence or complete dissolution of effervescent granules.

EXAMPLE 14

Preparation of Tablets Containing Effervescent Granules

The following general procedure can be used to prepare a wide variety of tablet dosage forms containing the effervescent granules of the invention. It should be understood that the ingredients listed below are merely representative and can be replaced by many other equivalent compounds. Any of the effervescent granules detailed here as granules A through S may be employed where effervescent granule (EG) is indicated in the following tablet formulations.

|    | Ingredients | Amount (% Wt.) |
|----|---|---|
| A. | | |
|    | Effervescent Granule (EG) | 40 |
|    | Dicalcium Phosphate | 10 |
|    | Microcrystalline Cellulose (MCC) | 5 |
|    | Calcium Stearate | 2.5 |
|    | Silicon Dioxide | 1.0 |
|    | APAP | 41.5 |
| B. | | |
|    | EG | 50 |
|    | Pseudoephedrine HCl | 20 |
|    | Mannitol | 29 |
|    | Magnesium Stearate | 0.5 |
|    | Silicon Dioxide | 0.5 |
| C. | | |
|    | EG | 25 |
|    | MCC | 15 |
|    | Diltiazem | 10 |
|    | Lactose | 47 |
|    | Magnesium Stearate | 0.5 |
|    | Silicon Dioxide | 0.5 |
|    | Aspartame | 1 |
|    | Grape Flavor | 1 |
| D. | | |
|    | APAP | 60 |
|    | EG (C) | 8 |
|    | Mannitol | 30 |
|    | Aspartame | 1.5 |
|    | Magnesium Stearate | 0.5 |
| E. | | |
|    | Aspirin | 50 |
|    | Mannitol | 15 |
|    | AVICEL PH 101 | 25.5 |
|    | Aspartame | 1.5 |
|    | Stearic Acid | 2 |
|    | EG (B) | 6 |
| F. | | |
|    | APAP | 55 |
|    | ACT-DI-SOL | 3 |
|    | EG (A) | 8 |
|    | AVICEL PH101 | 10 |
|    | Mannitol | 22 |
|    | Aspartame | 1.5 |
|    | Magnesium Stearate | 0.5 |
| G. | | |
|    | CPM | 1 |
|    | EG (A) | 8 |
|    | AVICEL PH101 | 26.5 |
|    | Mannitol | 62 |
|    | Magnesium Stearate | 0.5 |
|    | Aspartame | 2 |

(C) refers to EG made according to Example I using ingredients listed under C.

Table 3 is presented to demonstrate effervescing granules in a convenient dose form. In this table, the dose form is a tablet. However, any number of other dose forms may be employed in providing a patient ready therapeutic of the present granulations.

TABLE 3

Hot-Melt Extruded - Effervescent Couple
(Tablet Formulations)
Effervescent tablets contains effervescent
granules prepared by hot-melt extrusion.

| Tablet Formulation H % w/w | Excipient | Tablet Formulation I % w/w |
|---|---|---|
| 32.0 | APAP | 32.0 |
| 20.0 (formulation y) | EG | 25.0 (granulation s) |
| 28.0 | Mannitol, fine powder | 26.0 |
| 8.0 | Emcocel ® LM50 | 5.0 |
| 5.0 | Kollodion ® CL | 5.0 |
| 5.0 | Aspartame | 5.0 |
| 0.7 | Flavor, grape | 0.7 |
| 0.4 | Lake, lavender | 0.4 |
| 0.3 | Cab-O-Sil ® M5P | 0.3 |
| 0.6 | Magnesium Stearate | 0.6 |

Generally, the listed ingredients are thoroughly mixed in a low relative humidity environment to form a tableting mixture. All the ingredients will generally pass through a 20 mesh screen. The tableting mixture is tableted in a conventional tableting press.

EXAMPLE 15

Preparation of Effervescent Reconstitutable Dry Beverage Base

The following ingredients are thoroughly mixed in the amounts specified: Fries & Fries grapefruit flavoring #91470 (5.0 g), fructose USP (30.0 g), aspartame (0.5 g), and effervescent granule (2.0 g, prepared according to Example 1B). An active ingredient can optionally be added to this formulation. The above mixture will generally be reconstituted by adding water until solids reach 10% by weight of the final formulation.

EXAMPLE 16

Drug-Containing Hot Melt Extrudable Effervescent Granulations

The following examples are presented to demonstrate the utility of the present invention in the preparation of drug-containing granules. The drugs identified in Table 4 are for representative purposes only, as many other pharmacologically agents may be similarly included alone or in combination in the granulation process employing techniques known to those of ordinary skill in the art.

TABLE 4

| Drug-Containing Hot-Melt Extruded Effervescent Formulations | | | | | | |
|---|---|---|---|---|---|---|
| Ibuprofen | 50 | 50 | 0 | 0 | 0 | 30 |
| Chlorphesinamine Maleate | 0 | 0 | 5 | 5 | 0 | 5 |
| Pseudoephridine HCl | 0 | 0 | 0 | 25 | 20 | |
| AcDiSol | 5 | 5 | 0 | 0 | 5 | 5 |
| Microcrystalline Cellulose | 20 | 10 | 32 | 20 | | 5 |
| Na Bicarbonate | 13 | 13 | 15 | 18 | 20 | 15 |
| Citric Acid | 12 | 12 | 14 | 15 | 18 | 13 |
| PEG 3350 | 0 | 10 | 14 | 12 | 10 | 12 |
| Crosslinked PVP | 0 | 0 | 5 | 3 | 3 | 3 |
| Explotab | 0 | 0 | 0 | 2 | | 2 |
| Mannitol | 0 | 0 | 5 | | 9 | |
| Xylitol | 0 | 0 | 10 | | 15 | 10 |

EXAMPLE 17

Preparation of Effervescent Suspension

The following ingredients are thoroughly mixed in the amounts specified: effervescent granule (59 g), bentonite (35 g) and BENLATE (6 g, from E.I. DuPont). The resulting mixture is suspended by adding approximately 1000 ml of water prior to spraying.

It is contemplated that this preparation may be used for example as a spray suitable for application to plants. The instantaneous dispersion of active ingredients provided through use of the present formulations reduces caking and agglomeration of the active ingredient onto surfaces.

EXAMPLE 18

Tablets

The present example is presented to demonstrate the formulation of tablets from the granules described herein.

The granules provided herein may be compressed into tablets with the optional addition of lubricants, glidants, disintegrants, and other tablet excipients that are well known in the art.

After suitable processing of the granules to the desired particle size, the lubricants (e.g., 1%–1.5% @ stearic acid, magnesium stearate @ 0.05, Prv=Sodium stearyl fumarate @ 2%), glidants (talc, silicon dioxide, cabosil M5P) and/or other excipients (flavorants, disintegrants, colorants and anti-oxidants) that are known in the art, are blended prior to compression into tablets or other solid dosage forms known to those of skill in the art. These granulations may also be packaged for individual dosage use upon mixture with an appropriate liquid, such as water or other liquid vehicle suitable for ingestion.

The granules and tablets containing the granules of the invention may also include, by way of example, H2 antagonists (e.g., anitidine), cardiovascular drugs, (e.g., dilitizan hydrochloride), local anesthetic (e.g., lidocaine hydrochloride), anti fungal agent (e.g., miconazole), antibiotics (e.g., erythromycin), anti-cancer agents (coated for gastric release) (e.g., methotrexate), and tranquilizers (e.g. arnitryptoline).

EXAMPLE 19

Preparation of a Vaginal Tablet Comprising Slowly Effervescing Effervescent Granules One thousand layered tablets are prepared as follows:

(a) Miconazole: 300 gm (b) Hydroxypropylmethylcellulose (400 cps): 100.0 gm (c) Mannitol: 100.0 gm (d) Corn starch: 6.0 gm (e) Zinc stearate: 3.6 gm Effervescent granule (1E): 50 gm Using a suitable mixer, the miconazole, mannitol and Hydroxypropylmethylcellulose are mixed well via geometric dilution. The mixture is mixed in a Fitzmill quipped with a No. 000 screen and granulated using a 5% starch paste prepared by adding the corn starch to approximately 115 ml of water. Additional water is added as required to make a suitable granulation. The resulting granulation is wet-screened using a No. 2 screen and tray dried at 40° C. to 50° C. for 8 to 12 hours. The dried granulation is ground and passed through a No. 10 screen. Zinc stearate and effervescent granule, which has passed through a No. 20 screen, is added to the granulation, mixed well and the resulting slow release effervescent granulation reserved for tablet compression.

Using a suitable layer press, such as the Manesty Layer Press, the slow release granulation is added to the adjusted die cavity to provide a layer having a weight of approximately 500 mg. The final compression pressure is adjusted to provide a suitable tablet with a total weight of approximately 0.5 g.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

REFERENCES

The following references, to the extent they provide exemplary procedural or other details supplementary to those set forth herein, are specifically incorporated herein by reference.

| | | |
|---|---|---|
| 1. | U.S. Pat. No. 1,262,888 | (4/1918) to Westlake |
| 2. | U.S. Pat. No. 3,962,417 | (6/1976) to Howell |
| 3. | U.S. Pat. No. 4,613,497 | (9/1986) to Chaukin |
| 4. | U.S. Pat. No. 4,639,368 | (1/1987) to Niazi |
| 5. | U.S. Pat. No. 4,687,662 | (8/1987) to Schobel |
| 6. | U.S. Pat. No. 4,725,427 | (2/1988) to Ashmead |
| 7. | U.S. Pat. No. 4,753,792 | (6/1988) to Aberg |
| 8. | U.S. Pat. No. 4,940,588 | (7/1990) to Sparks |
| 9. | U.S. Pat. No. 5,055,306 | (2/1991) to Barry |
| 10. | U.S. Pat. No. 3,667,929 | (6/1972) to Fleming |
| 11. | U.S. Pat. No. 4,153,678 | (5/1979) to Quinlan |
| 12. | U.S. Pat. No. 4,267,164 | (5/1981) to Yeh et al. |
| 13. | U.S. Pat. No. 5,100,674 | (3/1992) to Ser et al. |
| 14. | U.S. Pat. No. 5,178,878 | |
| 15. | Pharmaceutical Dosage Forms-Tablets vol. 1, 2nd edition, Herbert A. Lieberman, ed. pp. 372–376. | |
| 16. | BE664197 | (11/1965) |
| 17. | EPo189114 | (7/1986) |
| 18. | EP0190689 | (8/1986) |
| 19. | EP0217631 | (4/1987) |
| 20. | DE1938709 | (4/1970) |
| 21. | DE2020893 | (11/1970) |
| 22. | DE2213604 | (6/1973) |
| 23. | GB917456 | (2/1963) |
| 24. | GB1055854 | (1/1967) |
| 25. | GB1276839 | (6/1972) |
| 26. | GB1300998 | (12/1972) |
| 27. | GB1370766 | (10/1974) |
| 28. | GB2019844 | (11/1979) |
| 29. | GB2083997 | (4/1982) |
| 30. | EP0396335 | (11/1990) |
| 31. | GB0003160 | (10/1872) |

What is claimed is:

1. A thermal heat process for preparing an effervescent granule formulation containing a pharmacologically active agent comprising:

combining an acidic agent, an alkaline agent, a hot-melt extrudable binder that forms a full or partial eutectic mixture with said acidic agent, and a pharmacologically active agent, dry blending said acidic agent, said alkaline agent, and said hot-melt extrudable binder to form a first mixture; and hot-melt extruding said mixture to form said effervescent granules having a controllable rate of effervescence.

2. An effervescent granule having a controllable rate of effervescence comprising:

a mixture consisting essentially of an acidic agent, a pharmacologically active agent, and a hot-melt extrudable binder; and an alkaline agent;

the effervescent granule being made by a water free and a solvent free thermal heat process comprising:
dry blending said mixture; and
hot-melt extruding said blended mixture to form an effervescent granule.

3. The thermal heat process of claim 1 wherein the pharmacologically active agent is a narcotic.

4. The thermal heat process of claim 3, wherein the narcotic is a phenanthrene derivative.

5. The thermal heat process of claim 4, wherein the phenanthrene derivative is morphine sulfate.

6. The thermal heat process of claim 1, wherein the pharmacologically active agent is a synthetic anti-diarrheal agent.

7. The thermal heat process of claim 6, wherein the synthetic anti-diarrheal agent is loperamide hydrochloride.

8. The thermal heat process of claim 1, wherein the pharmacologically active agent is an antiviral agent.

9. The thermal heat process of claim 8, wherein the antiviral agent is acyclovir.

10. The thermal heat process of claim 1, wherein the pharmacologically active agent is an anxiolytic agent.

11. The thermal heat process of claim 10, wherein the anxiolytic agent is buspirone.

12. The thermal heat process of claim 1, wherein the pharmacologically active agent is a diuretic agent.

13. The thermal heat process of claim 12, wherein the diuretic agent is hydrochlorthiazide.

14. The thermal heat process of claim 3, wherein the narcotic is a morphine derivative.

15. The thermal heat process of claim 14, wherein the morphine derivative is hydromorphone hydrochloride.

16. The thermal heat process of claim 1, wherein the pharmacologically active agent is an antidepressant.

17. The thermal heat process of claim 16, wherein the antidepressant is fluoxetine hydrochloride.

18. The thermal heat process of claim 1, wherein the pharmacologically active agent is a serotonin agonist.

19. The thermal heat process of claim 17, wherein the serotonin agonist is sumatriptan succinate.

20. The thermal heat process of claim 1, wherein the pharmacologically active agent is a levorotatory isomer of thyroxin.

21. The thermal heat process of claim 20, wherein the levorotatory isomer is levothyroxine sodium.

22. The thermal heat process of claim 1, wherein the pharmacologically active agent is a cholesterol lowering agent.

23. The thermal heat process of claim 22, wherein the cholesterol lowering agent is simvastatin.

24. The thermal heat process of claim 1, wherein the pharmacologically active agent is an alpha adrenergic blocking agent.

25. The thermal heat process of claim 24, wherein the alpha adrenergic blocking agent is ergotamine tartrate.

26. The thermal heat process of claim 4, 6, 8, 10, 12, 14, 16, 18, 20, 22, or 24, wherein the effervescent granules are formulated into a tablet.

27. The effervescent granule of claim 2, wherein the pharmacologically active agent is a phenanthrene derivative.

28. The effervescent granule of claim 27, wherein the phenanthrene derivative is morphine sulfate.

29. The effervescent granule of claim 2, wherein the pharmacologically active agent is a synthetic anti-diarrheal agent.

30. The effervescent granule of claim 2, wherein the pharmacologically active agent anti-diarrheal agent is loperamide hydrochloride.

31. The effervescent granule of claim 2, wherein the pharmacologically active agent is an antiviral agent.

32. The effervescent granule of claim 31, wherein the antiviral agent is acyclovir.

33. The effervescent granule of claim 2, wherein the pharmacologically active agent is an anxiolytic agent.

34. The effervescent granule of claim 33, wherein the anxiolytic agent is buspirone.

35. The effervescent granule of claim 2, wherein the pharmacologically active agent is a diuretic agent.

36. The effervescent granule of claim 35, wherein the diuretic agent is hydrochlorthiazide.

37. The effervescent granule of claim 2, wherein the narcotic is a morphine derivative.

38. The effervescent granule of claim 37, wherein the morphine derivative is hydromorphone hydrochloride.

39. The effervescent granule of claim 2, wherein the pharmacologically active agent is an antidepressant.

40. The effervescent granule of claim 39, wherein the antidepressant is fluoxetine hydrochloride.

41. The effervescent granule of claim 2, wherein the pharmacologically active agent is a serotonin agonist.

42. The effervescent granule of claim 41, wherein the serotonin agonist is sumatriptan succinate.

43. The effervescent granule of claim 2, wherein the pharmacologically active agent is a levorotatory isomer of thyroxin.

44. The effervescent granule of claim 43, wherein the levorotatory isomer is levothyroxine sodium.

45. The effervescent granule of claim 2, wherein the pharmacologically active agent is a cholesterol lowering agent.

46. The effervescent granule of claim 45, wherein the cholesterol lowering agent is simvastatin.

47. The effervescent granule of claim 1, wherein the pharmacologically active agent is an alpha adrenergic blocking agent.

48. The effervescent granule of claim 46, wherein the alpha adrenergic blocking agent is ergotamine tartrate.

49. The effervescent granule of claim 26, 28, 30, 32, 34, 36, 38, 40, 42, 44, or 46, wherein the effervescent granule is formulated into a tablet.

50. The effervescent granule of claim 2 that also contains an antioxidant.

51. The effervescent granule of claim 2 wherein the mixture includes a plasticizer.

52. The thermal heat process of claim 1 wherein the effervescent formulation includes a plasticizer.

* * * * *